United States Patent
Reber et al.

[19]

[11] Patent Number: 5,950,632
[45] Date of Patent: Sep. 14, 1999

[54] MEDICAL COMMUNICATION APPARATUS, SYSTEM, AND METHOD

[75] Inventors: William L. Reber, Schaumburg, Ill.; Cary D. Perttunen, Shelby Township, Mich.

[73] Assignee: Motorola, Inc., Schaumburg, Ill.

[21] Appl. No.: 08/811,081

[22] Filed: Mar. 3, 1997

[51] Int. Cl.⁶ ....................................................... H04Q 1/30
[52] U.S. Cl. .......................... 128/898; 128/903; 128/904; 128/920; 340/311.1; 340/825.44; 455/31.3
[58] Field of Search ..................................... 128/897, 903, 128/904, 920, 921–925; 340/311.1, 286.01, 825.44, 825.47; 455/31.3, 228; 600/300, 301, 529

[56] References Cited

U.S. PATENT DOCUMENTS

| | | |
|---|---|---|
| 4,458,693 | 7/1984 | Badzinski et al. . |
| 4,819,860 | 4/1989 | Hargrove et al. . |
| 4,827,943 | 5/1989 | Bornn et al. . |
| 4,838,275 | 6/1989 | Lee . |
| 4,856,047 | 8/1989 | Saunders . |
| 4,857,716 | 8/1989 | Gombrich et al. ................. 340/825.34 |
| 4,974,607 | 12/1990 | Miwa . |
| 5,003,984 | 4/1991 | Muraki et al. . |
| 5,016,172 | 5/1991 | Dessertine .......................... 364/413.02 |
| 5,019,974 | 5/1991 | Beckers .............................. 364/413.02 |
| 5,257,627 | 11/1993 | Rapoport . |
| 5,307,263 | 4/1994 | Brown ................................ 364/413.09 |
| 5,319,355 | 6/1994 | Russek . |
| 5,339,821 | 8/1994 | Fujimoto . |
| 5,372,133 | 12/1994 | Hogen Esch . |
| 5,390,238 | 2/1995 | Kirk et al. .............................. 128/904 |
| 5,458,123 | 10/1995 | Unger . |
| 5,553,609 | 9/1996 | Chen et al. ............................. 128/904 |
| 5,594,786 | 1/1997 | Chaco et al. ........................... 128/904 |
| 5,623,242 | 4/1997 | Dawson, Jr. et al. ............. 340/829.19 |
| 5,710,551 | 1/1998 | Ridgeway .......................... 340/870.09 |
| 5,804,803 | 9/1998 | Cragun et al. . |
| 5,827,180 | 10/1998 | Goodman ................................ 600/300 |

OTHER PUBLICATIONS

Consumer Reports, Oct., 1996 "Blood–Glucose Meters—They're small, fast, and reliable," pp. 53–55.

"Electronic Measurement of Fluid Level Using Acoustic Sensors" by Bruce E. Stuckman et al., Proceedings of the 32nd Midwest Symposium on Circuits and Systems, Champaign–Urban, Illinois, Aug. 1989.

"Data Modeling for Healthcare Systems Integration: Use of the Metamodel" by Jack E. Myers, Toward An Electronic Patient Record '96 Conference & Exposition, Medical Records Institute, pp. 1–12.

"Integrating Medication Management into the Electronic Patient Record" by Steve W. Kelso et al., Toward An Electronic Patient Record '96 Conference & Exposition, Medical Records Institute, pp. 1–12.

"Meta Script" Brochure, The Prescription for Medication Management, Metadata® Information Partners, 4647 Long Beach Blvd., Suite C4, Long Beach, CA 90805–6979.

"Metadata—Integrated Repository (IP)" Brochure, Metadata® Information Partners, 4647 Long Beach Blvd., Suite C4, Long Beach, CA 90805–6979.

"Metadata—DataSchema" Brochure, Metadata® Information Partners, 4647 Long Beach Blvd., Suite C4, Long Beach, CA 90805–6979.

(List continued on next page.)

*Primary Examiner*—Michael Peffley
*Assistant Examiner*—David M. Ruddy
*Attorney, Agent, or Firm*—Jeffrey G. Toler; James E. Gauger

[57] ABSTRACT

A medical communication apparatus comprises a receiver (54) to receive a message and at least one output device (56) responsive to the receiver (54). The at least one output device (56) generates an alert for taking a first medicine and a second medicine in response to the message, and graphically indicates the first medicine and the second medicine.

8 Claims, 5 Drawing Sheets

OTHER PUBLICATIONS

"Metadata—DataConvert" Brochure, Metadata® Information Partners, 4647 Long Beach Blvd., Suite C4, Long Beach, CA 90805–6979.

"Metadata—Unified Database Management System (UDMS)" Brochure, Metadata® Information Partners, 4647 Long Beach Blvd., Suite C4, Long Beach, CA 90805–6979.

"Metadata—NetFax" Brochure, Metadata® Information Partners, 4647 Long Beach Blvd., Suite C4, Long Beach, CA 90805–6979.

"Metadata—Metamodel" Brochure, Metadata® Information Partners, 4647 Long Beach Blvd., Suite C4, Long Beach, CA 90805–6979.

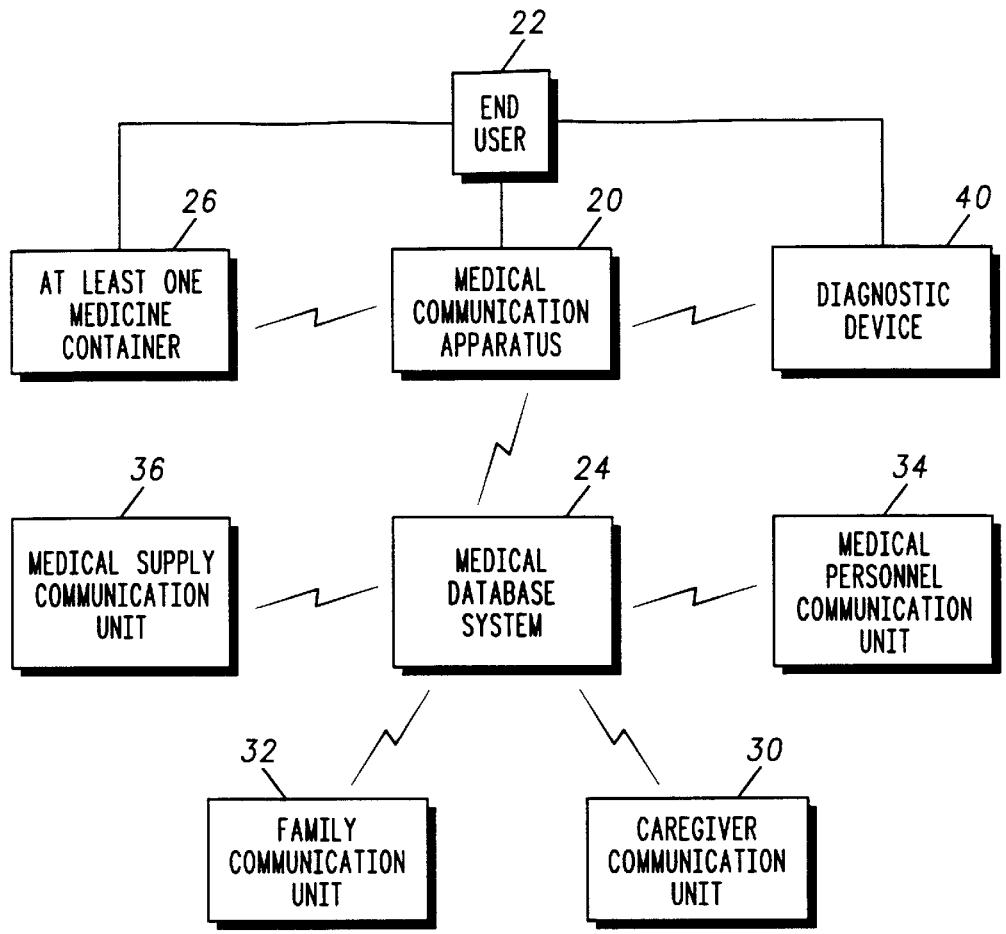
FIG.1
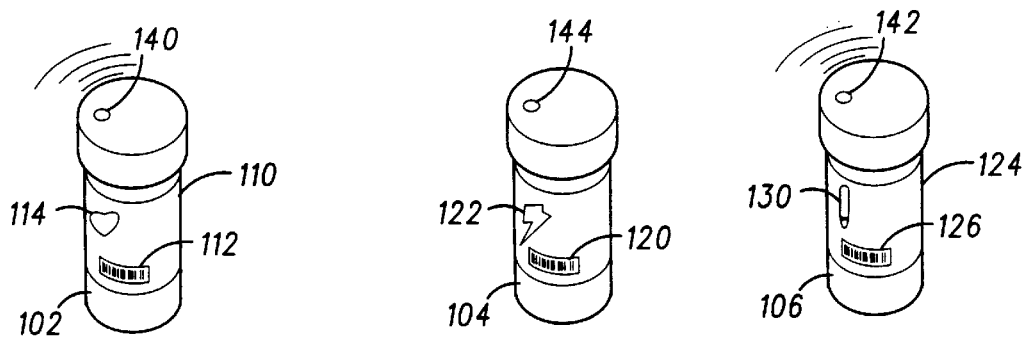
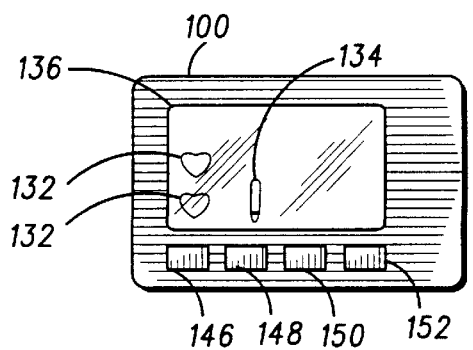
FIG.3

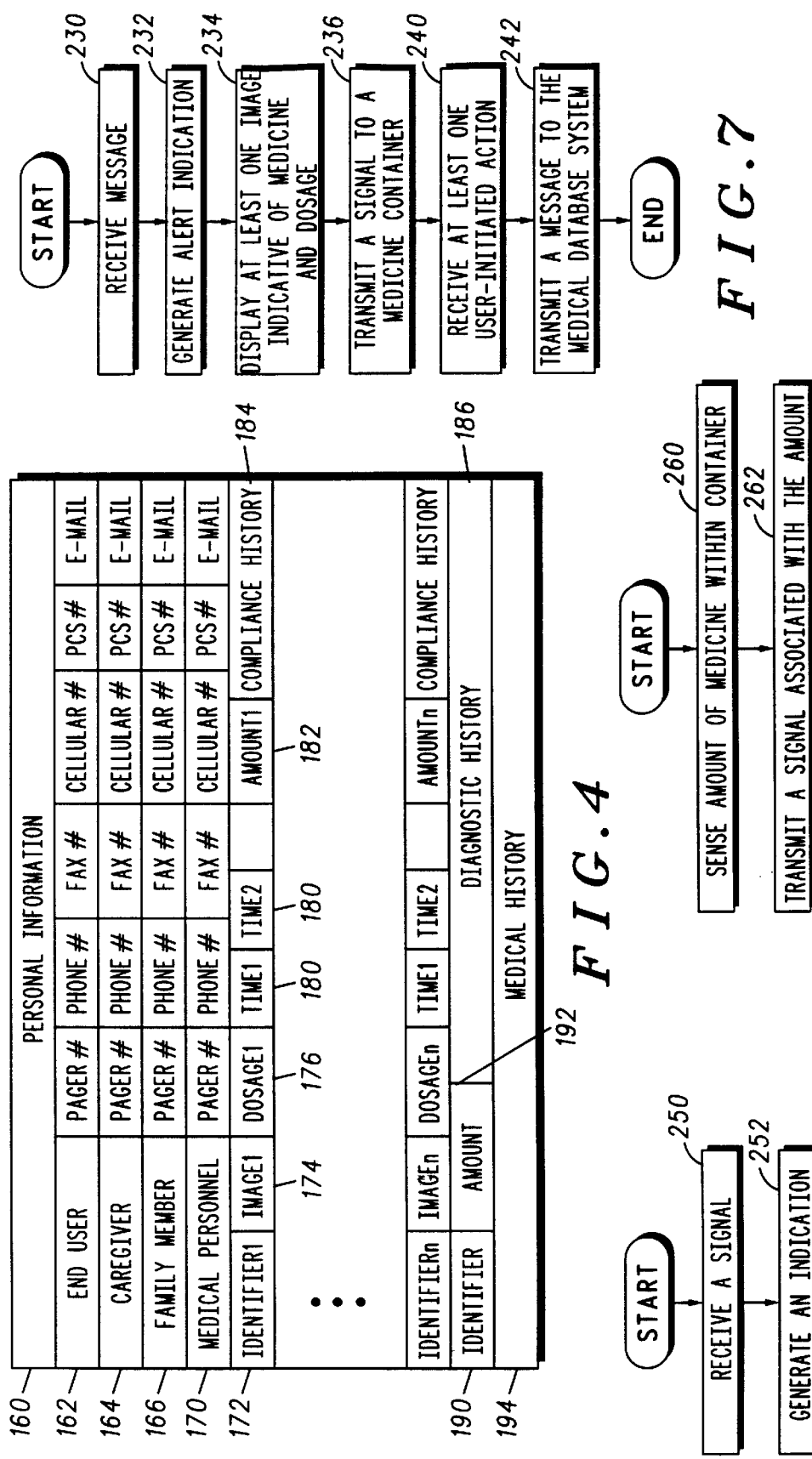

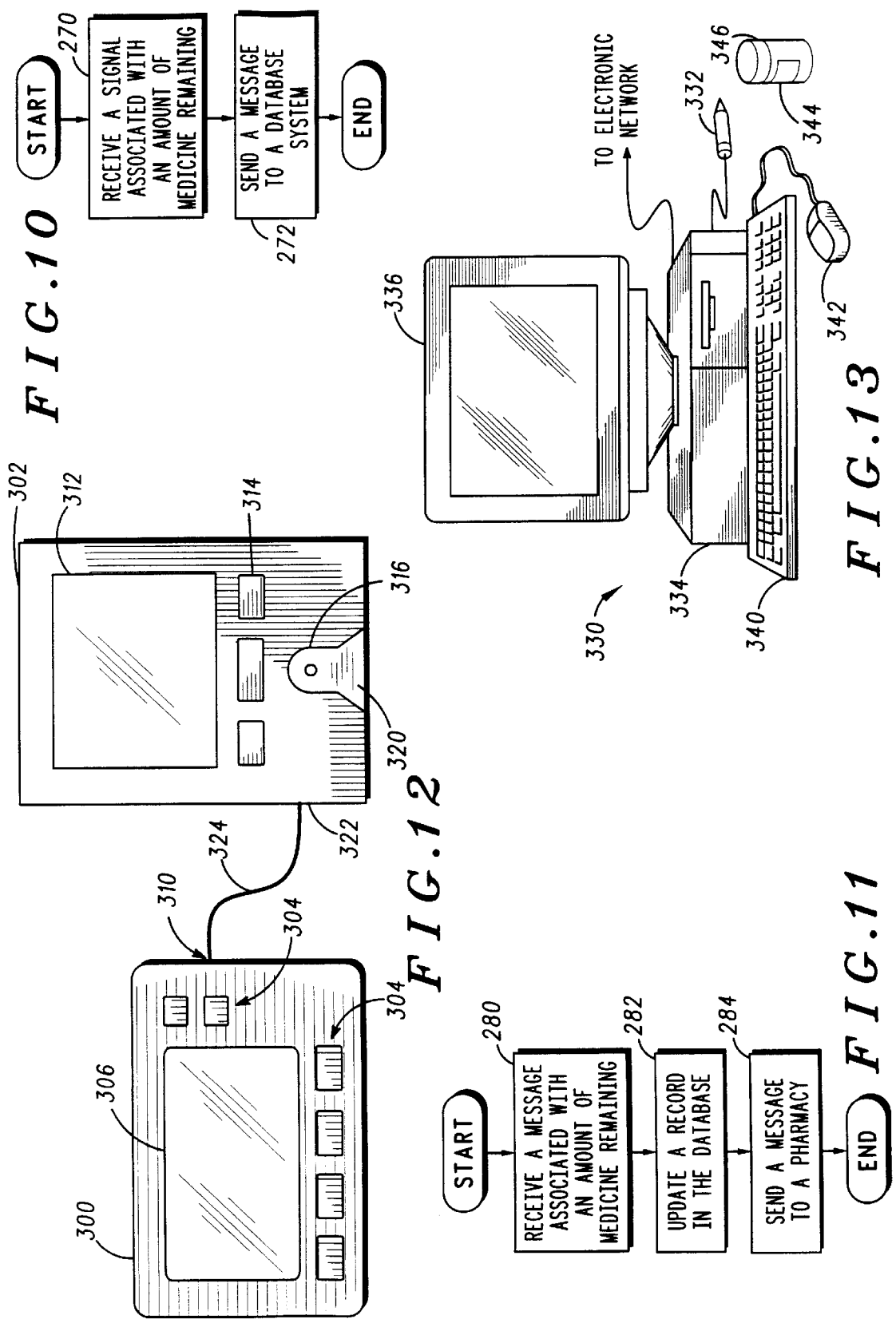

MEDICAL COMMUNICATION APPARATUS, SYSTEM, AND METHOD

RELATED APPLICATIONS

The present application is related to the following applications which are assigned to the same assignee as the present application:

"Electronic Network Navigation Device and Method for Linking to an Electronic Address Therewith", having Docket No. MNE00487 and U.S. Ser. No. 08/710,820, filed Sep. 23, 1996;

"Methods and Systems for Providing a Resource in an Electronic Network", having Docket No. MNE00490 and U.S. Ser. No. 08/726,004, filed Oct. 4, 1996;

"An Apparatus for Reading an Electronic Network Navigation Device and a Peripheral for Use Therewith", having Docket No. MNE00493 and U.S. Ser. No. 08/732,956, filed Oct. 17, 1996; and "Method, System, and Article of Manufacture for Producing a Network Navigation Device", having Docket No. MNE00494 and U.S. Ser. No. 08/744,338, filed Nov. 7, 1996.

The subject matter of the above-identified related applications is hereby incorporated by reference into the disclosure of this application.

TECHNICAL FIELD

The present invention relates to methods and systems for communicating medical information.

BACKGROUND OF THE INVENTION

Many individuals are required to regularly take multiple types of medicine at multiple times of a day. A number of difficulties are encountered in these situations, both for the individual taking the medicine and for those associated with the welfare of the individual.

Some difficulties result from the labeling of medicine containers. For some individuals, prescription labels on medicine containers are difficult to read and/or difficult to understand. This results from any combination of: (i) a small font size with which prescription labels are printed; (ii) laconic instructions printed on prescription labels; and (iii) unfamiliar words which identify the medicine in a container. Consequently, some individuals encounter difficulties such as determining the prescribed dosage of the medicine, and determining the times of the day to take the medicine. This can lead to errors in complying with a prescription.

Other difficulties are witnessed when an individual attempts to comply with one or more prescriptions. From time to time, the individual can forget to take his/her medicine. Further, the individual may fail to take the entire prescribed dosage. Additionally, the individual may forget where a medicine container is located. Further difficulties are produced as a result of drug interaction. Here, an individual can have an adverse reaction to two or more drugs which, if taken individually, would not occur. The aforementioned difficulties can result in anxiety and stress as an individual attempts to comply with his/her prescriptions.

BRIEF DESCRIPTION OF THE DRAWINGS

The invention is pointed out with particularity in the appended claims. However, other aspects of the invention are described in the following detailed description in conjunction with the accompanying drawings in which:

FIG. 1 is a block diagram of an embodiment of a medical communication system in accordance with the present invention;

FIG. 3 is an illustration of an embodiment of a medical communication apparatus which assists an end user in complying with three prescriptions;

FIG. 4 is an illustration an embodiment of a record for the end user which is maintained by the medical database system;

FIG. 7 is a flow chart of an embodiment of a first method performed by the medical communication apparatus;

FIG. 8 is a flow chart of an embodiment of a first method performed by the medicine container;

FIG. 9 is a flow chart of an embodiment of a second method performed by the medicine container;

FIG. 10 is a flow chart of an embodiment of a second method performed by the medical communication apparatus;

FIG. 11 is a flow chart of an embodiment of a third method performed by the medical database system;

FIG. 12 is an illustration of an embodiment of a medical communication apparatus coupled to a diagnostic device; and FIG. 13 is an illustration of an embodiment of a medical communication apparatus coupled to a data reader.

DETAILED DESCRIPTION OF A PREFERRED EMBODIMENT

Figure 2:
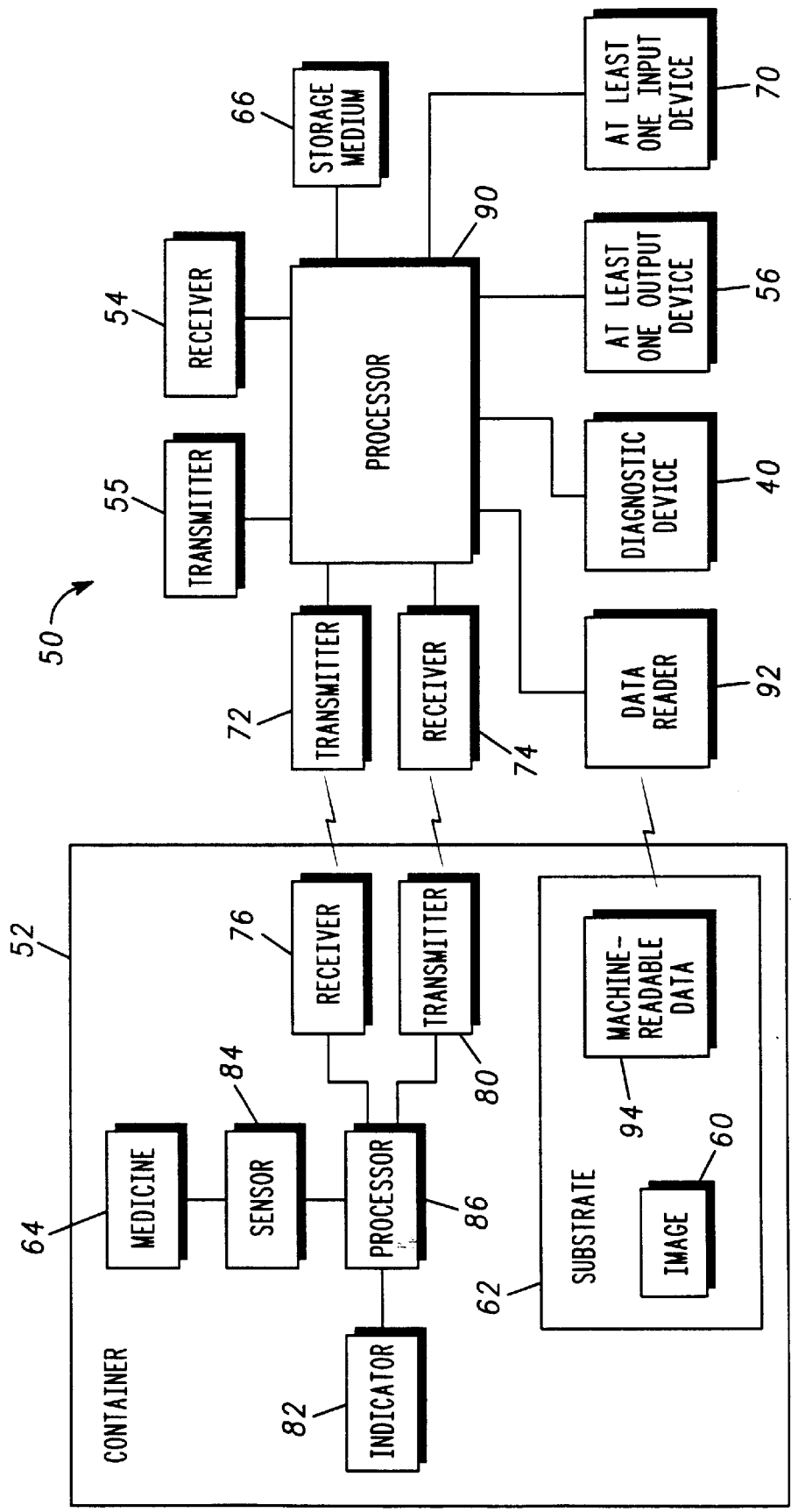
FIG. 2 is a block diagram of an embodiment of a medical communication apparatus and a medicine container in accordance with the present invention.

FIG. 1 is a block diagram of an embodiment of a medical communication system in accordance with the present invention. The medical communication system includes a medical communication apparatus 20 for an end user 22. The medical communication apparatus 20 assists the end user 22 in complying with at least one prescription for taking medicine. The at least one prescription can include a plurality of prescriptions for a plurality of medicines to be taken at a plurality of times of each day by the end user 22.

The medical communication apparatus 20 communicates with a medical database system 24. The medical database system 24 stores information associated with the at least one prescription for the end user 22. Examples of the information stored by the medical database system 24 include, but are not limited to, a name of each medicine which the end user 22 is prescribed to take, a dosage of each medicine, times that each medicine is to be taken, an amount of each medicine which remains in a prescription, and an image or an indicator thereof associated with each medicine.

The medical database system 24 communicates with the medical communication apparatus 20 to alert the end user 22 of a time to take at least one medicine. The alert can be in the form of an audible indication, a visible indication, or a vibratory indication generated by the medical communication apparatus 20. In addition, the medical communication apparatus 20 can indicate which medicine to take, and a corresponding amount of each medicine to take.

Preferably, the medical communication apparatus 20 communicates with at least one medicine container 26 containing the at least one medicine which is to be taken. Here, the medical communication apparatus 20 transmits a signal to the at least one medicine container 26. Selected medicine containers generate an audible indication or a visible indication in response to receiving the signal. The indication is beneficial in aiding the end user 22 to locate selected medicine containers at times when medicine contained therein is to be taken.

After being alerted, the medical communication apparatus 20 communicates a signal to the medical database system 24 to acknowledge that the end user 22 has complied with his/her prescription. If no acknowledgment is received or if an improper acknowledgment is received (e.g. indicating that an improper medicine was taken and/or an improper dosage was taken), the medical database system 24 can either: (i) communicate a subsequent signal to the medical communication apparatus 20 and/or to another communication unit associated with the end user 22; (ii) communicate a signal indicating noncompliance to a communication unit 30 associated with a caregiver of the end user 20; (iii) communicate a signal indicating noncompliance to a communication unit 32 associated with a family member of the end user 20; and/or (iv) communicate a signal indicating noncompliance to a communication unit 34 associated with medical personnel for the end user 20.

Examples of the communication units 30, 32, and 34 include but are not limited to: a telephone; a fax machine; a cellular telephone; a pager; a personal communication services unit; and an electronic network access apparatus such as a modem-equipped personal computer, an Internet television, or a network computer. The medical database system 24 can communicate with the communication units 30, 32, and 34 by a telephone call, a fax, a paging message, or an electronic mail message, for example.

Optionally, the at least one medicine container 26 senses an amount of medicine remaining therein, and transmits a signal associated therewith to the medical communication apparatus 20. In turn, the medical communication apparatus 20 communicates a signal associated with the amount of medicine remaining to the medical database system 24. The medical database system 24 communicates with a communication unit 36 associated with a medical supply source, such as a pharmacy, based upon the amount of medicine remaining. For example, the medical database system 24 can communicate a message to a pharmacy when the amount of medicine is at or below a predetermined threshold. This is beneficial for automatic renewal of prescriptions when the amount of medicine is below the predetermined threshold.

The medical database system 24 is populated by communicating with the communication unit 34 of the medical personnel and/or the communication unit 36 associated with the medical supply source. Upon prescribing a medicine, either the medical personnel or a pharmacy can communicate an identifier of the end user 22, the name of the medicine, the dosage, the times for taking the medicine, and an image indicative of the medicine to the medical database system 24.

Optionally, the medical communication apparatus 20 is capable of communicating data with a diagnostic device 40. The diagnostic device 40 monitors a condition of the end user 22 and communicates a signal representative thereof to the medical communication apparatus 20. Examples of the diagnostic device 40 include, but are not limited to, a blood glucose meter, a blood pressure monitor, an electronic thermometer, and an electronic scale. The medical communication apparatus 20 communicates the diagnostic data to the medical database system 24. The medical database system 24, in turn, stores information based on the diagnostic data in a record for the end user 22.

The medical database system 24 can estimate or maintain a count of an amount of a medical supply for the end user 22. Examples of the medical supply include, but are not limited to, strips for a glucose device, lancets, and needles. The medical database system 24 communicates with the communication unit 36 associated with the medical supply source based upon the amount of the medical supply which remains. For example, the medical database system 24 can communicate a message to the medical supply source when the amount of the medical supply is at or below a predetermined threshold. This is beneficial for automatic reordering of medical supplies for the end user 22.

Preferably, the medical database system 24 includes a computer system having a storage device to maintain a database of records for end user 22 and other end users. The computer system is linked to at least one network such as a paging network, an electronic network, a cable television network, and/or a telephone network to communicate with the medical communication apparatus 20 and the communication units 30, 32, 34 and 36. Preferably, communication is encrypted between the medical database system 24 and each of the medical communication apparatus 20 and the communication units 30, 32, 34, and 36.

FIG. 2 is a block diagram of an embodiment of a medical communication apparatus 50 and a medicine container 52 in accordance with the present invention. The medical communication apparatus 50 includes a receiver 54 and an optional transmitter 55 to communicate with the medical database system 24. Preferably, the receiver 54 is included in a selective call receiver, such as a wireless pager, to communicate with the medical database system 24 via a paging service. The receiver 54 can be included in a one-way pager (receive-only) or can be included with the transmitter 55 in a two-way pager (receive and transmit). The paging service can utilize a local paging network, a regional paging network, a nationwide paging network, or a global paging network.

It is noted that the receiver 54 and the transmitter 55 can have a variety of other embodiments. For example, the receiver 54 and the transmitter 55 can be included as parts of a modem, a telephone, a cellular telephone, or a network adapter. In general, the receiver 54 and the transmitter 55 communicates with the medical database system 24 by a network such as a telephone network, a computer network, or a cable television network.

The medical communication apparatus 50 further includes at least one output device 56 responsive to the receiver 54. The at least one output device 56 is utilized to alert an end user to take at least one medicine in response to a paging message received by the receiver 54. Examples of the at least one output device 56 include but are not limited to: a display device such as a liquid crystal display to provide a visible alert; an audio output device such as a speaker or a piezoelectric transducer to provide an audible alert; and a vibratory device to provide a vibratory alert.

Additionally, the at least one output device 56 is utilized to indicate which medicine to take, and how much of each medicine to take. Preferably, the at least one output device 56 includes a display device which displays a graphical representation of each medicine to take. The graphical representation can include an image corresponding to an image 60 associated with the medicine container 52. The image 60 can be supported by a substrate 62 which is affixed to the medicine container 52 or is a part of the medicine container 52. Alternatively, the graphical representation can include an image of medicine 64 within the medicine container 52. Here, for example, the graphical representation can include an image of a pill. If desired, the graphical representation can include a color corresponding to a color associated with the medicine container 52 or the medicine 64.

Regardless of the type of graphical representation, it is preferred that the at least one output device 56 also indicate a dosage of each medicine which is to be taken. The dosage can be indicated numerically by displaying a number with the graphical representation. Alternatively, the dosage can be indicated by displaying a number of like graphical representations. For example, a dosage of two pills can be indicated by displaying two graphical representations for the pill.

The graphical representation and the dosage can be included in the paging message received by the receiver 54. Alternatively, the graphical representation and/or the dosage can be locally stored in a storage medium 66. Here, the paging message can include a designator of a prestored image stored by the storage medium 66.

As another alternative, the graphical representation is hardwired into the display device 56. Here, for example, each of a plurality of predetermined graphical images is patterned into the display device as a respective display element. Each of the predetermined graphical images is independently activated and deactivated in response to the paging message.

Optionally, the medical communication apparatus 50 further includes at least one input device 70. In response to a user-initiated action received by the at least one input device 70, the transmitter 55 transmits a signal to acknowledge compliance with the prescription. The signal is communicated to the medical database system 24 via a paging service. Examples of the at least one input device 70 include but are not limited to one or more buttons, a touchpad, a touchscreen, a pointing device, a trackball, and a mouse.

Optionally, the medical communication apparatus 50 includes a transmitter 72 and a receiver 74 for communicating signals with a receiver 76 and a transmitter 80 associated with the medicine container 52. In response to the receiver 54 receiving a paging message indicating that the medicine 64 is to be taken, the transmitter 72 transmits a signal for reception by the receiver 76. An indicator 82 generates an indication, such as an audible indication or a visible indication, in response to the receiver 76 receiving the signal. The indicator 82 can include a display device having a light-emitting display element or a liquid crystal display element to generate a visible indication, or an audio output device such as a speaker or a buzzer to generate an audible indication.

Alternatively, the transmitter 72 transmits the 35 signal to the receiver 76 in response to a user-initiated action received by the at least one input device 70. Here, for example, the end user 22 can depress a button to initiate an indication to be generated by the indicator 82.

Optionally, a sensor 84 is utilized to sense an amount of the medicine 64 which remains within the medicine container 52. In a preferred embodiment, the sensor 84 includes a transducer which generates a pressure wave in the medicine container 52. The transducer can include a piezoelectric transducer mounted to a cap of the medicine container 52. The amount of the medicine 64 in the medicine container 52 is estimated by sensing how the pressure wave is influenced thereby. For example, the amount of the medicine 64 can be sensed by either: (i) sensing a change in a frequency response exhibited by the piezoelectric transducer or a receiving transducer such as a microphone; or (ii) sensing a change in a transient response exhibited by the piezoelectric transducer or the receiving transducer.

The transmitter 80 transmits a signal based upon the amount of the medicine 64 sensed by the sensor 84. The signal can indicate the amount of the medicine 64 that remains, or can indicate that the amount of the medicine 64 is at or below a predetermined threshold. For example, the signal may be transmitted only if the amount of the medicine 64 is less than that required for a couple of days of use.

The signal from the transmitter 80 is received by the receiver 74. In response to receiving the signal, the transmitter 55 transmits a signal associated with the amount of the medicine 64. The signal is communicated to the medical database system 24 via the paging network. The signal can indicate the amount of the medicine 64 that remains, or can indicate that the amount of the medicine 64 is at or below a predetermined threshold.

It is preferred that the transmitter 72 and the receiver 76 communicate wirelessly, and that the transmitter 80 and the receiver 74 communicate wirelessly. Wireless communication can be facilitated using radio frequency transmitters and receivers, infrared transmitters and receivers, or ultrasonic transmitters and receivers, for example.

The receiver 76, the transmitter 80, the indicator 82, and the sensor 84 are coupled to a processor 86. The processor 86 directs operations performed by the aforementioned components using one or more electronic components such as a microprocessor, a custom integrated circuit, an application-specific integrated circuit, and/or discrete electronic components.

The receiver 54, the transmitter 55, the at least one output device 56, the storage medium 66, the at least one input device 70, the transmitter 72, and the receiver 74 are coupled to a processor 90. The processor 90 directs operations performed by the aforementioned components using one or more electronic components such as a microprocessor, a custom integrated circuit, an application-specific integrated circuit, and/or discrete electronic components.

Optionally, a data reader 92 is utilized to read machine-readable data 94 supported by the substrate 62. The machine-readable data 94 includes at least one of: data identifying the end user 22; data identifying the medicine 64; data for obtaining information about the medicine 64; data identifying a pharmacy from which the medicine 64 was procured; data for establishing a communication link with the pharmacy; data identifying medical personnel which prescribed the medicine 64; and data for establishing a communication link with the medical personnel.

The data identifying the end user 22 can include the name of the end user, an identification code, an insurance number, or a Social Security Number, for example. The data identifying the medicine 64 can include the name of the medicine or an identification code for the medicine 64.

The data for obtaining information about the medicine 64 can include data for linking to a resource in an electronic network. The resource provides downloadable information about the medicine 64, such as potential side effects and adverse interactions with other drugs. In one embodiment, the resource is provided by the medical database system 24. Here, the data commands the transmitter 55 to communicate a message to the medical database system 24 via a paging network. Thereafter, the medical database system 24 communicates information about the medicine 64 via a paging message. The information can be displayed using a display device associated with the medical communication apparatus 50.

In another embodiment, the resource is located on the Internet, the World Wide Web, or an intranet. In these cases, the data includes an electronic address which identifies the resource. The electronic address can include at least a portion of, or all of, a URL (Uniforn Resource Locator) or an IP (Internet Protocol) address, for example.

The data identifying the pharmacy from which the medicine 64 was procured can include the name of the pharmacy and/or an identification code for the pharmacy.

The data for establishing a communication link with the pharmacy can include a telecommunication number and/or an electronic address for the pharmacy. Examples of the telecommunication number include, but are not limited to, a telephone number and a pager identification number. Examples of the electronic address for linking to the pharmacy include but are not limited to an electronic mail address, a URL, and an IP address.

The data identifying the medical personnel that prescribed the medicine 64 can include the name of a doctor, an identification code for the doctor, the name of a medical center such as a hospital, and an identification code for the medical center.

The data for establishing a communication link with the medical personnel can include a telecommunication number such as a telephone number or a pager identification number, and/or an electronic address such an electronic mail address, a URL, or an IP address.

Preferably, the machine-readable data 94 is a printed code such as a one-dimensional bar code or a two-dimensional bar code. Examples of one-dimensional bar codes include, but are not limited to, 3 of 9, UPC-A, Code 128, Codabar, MSI, Extended 3 of 9, Code 93, Extended Code 93, Industrial 2 of 5, Standard 2 of 5, Code 11, and UCC/EAN-128. Examples of two-dimensional bar codes include, but are not limited to, Data Matrix and PDF417. In these embodiments, the data reader 92 includes an optical reading device such as a bar code reader.

Alternatively, the machine-readable data 94 is stored in and accessed from a radio frequency tag associated with the medicine container 52. Here, the data reader 92 includes a tag communicating device.

As another option, the diagnostic device 40 either is integrated with the medical communication apparatus 50 or is a peripheral of the medical communication apparatus 50. The diagnostic device 40 communicates diagnostic data measured thereby for storage in the storage medium 66 and/or for communication to the medical database system 24 via the transmitter 55.

FIG. 3 is an illustration of an embodiment of a medical communication apparatus 100 which assists an end user in complying with three prescriptions. The medical communication apparatus 100 can be embodied by a two-way pager, such as a Tango™ pager by Motorola, Inc.

The three prescriptions include a first medicine contained in a first medicine container 102, a second medicine contained in a second medicine container 104, and a third medicine contained in a third medicine container 106. The first medicine container 102 includes a label 110 which supports machine-readable data 112 and a human-readable image 114 associated with the first medicine. The second medicine container 104 includes a label 116 which supports machine-readable data 120 and a human-readable image 122 associated with the second medicine. The third medicine container 106 includes a label 124 which supports machine-readable data 126 and a human-readable image 130 associated with the third medicine.

For purposes of illustration, the human-readable image 114 includes a heart-shaped icon to indicate to the end user 22 that the first medicine is for a heart condition. The human-readable image 122 includes an icon indicating that the second medicine is for alleviating pain. The human-readable image 130 includes an image of a pill of the third medicine.

At a time when the end user 22 is prescribed to take two pills of the first medicine and one pill of the third medicine, the medical communication apparatus 100 displays two images 132 of the human-readable image 114 and one image 134 of the human-readable image 130. The two images 132 and the one image 134 are displayed by a display device 136 in response to a paging message received by the medical communication apparatus 100.

A first display element of the display device can be patterned as one of the two images 132, a second display element can be patterned as another of the two images 132, and a third display element can be patterned as the image 134. Alternatively, each of the two images 132 and the image 134 can be formed by selectively activating a plurality of pixels in an array of display elements.

The medical communication apparatus 100 transmits a first signal for reception by a receiver associated with the first medicine container 102, and a second signal for reception by a receiver associated with the third medicine container 106. The first signal directs an audio output device 140 associated with the first medicine container 102 to generate an audible indication. The second signal directs an audio output device 142 associated with the third medicine container 106 to generate an audible indication. The audible indications assist the end user 22 to determine which medicines to take, and to locate the first medicine container 102 which is remotely located from the second medicine container 104 and the third medicine container 106.

It is noted that an audible indication is not generated by an audio output device 144 associated with the second medicine container 104 since the second medicine is not to be taken at this time. However, the display device 136 is capable of displaying an image corresponding to the human-readable image 122 at another time. The image can be displayed by a plurality of pixels, or by a display element patterned as the human-readable image 122.

The medical communication apparatus 100 includes at least one input device such as a first button 146, a second button 148, a third button 150, and a fourth button 152. In general, the at least one input device can include any plurality of buttons.

The end user depresses the first button 146 to indicate he/she has complied with taking the first medicine, and depresses the second button 148 to indicate he/she has complied with taking the third medicine. In response to depressing the first button 146 and the second button 148, the medical communication apparatus 100 communicates an acknowledgment signal to the medical database system 24 via a paging network.

FIG. 4 is an illustration of an embodiment of a record for the end user which is maintained by the medical database system 24. Typically, the medical database system 24 maintains a plurality of records for a plurality of end users served thereby.

The record includes personal information 160 about the end user. The personal information 160 can include the name of the end user, an address of the end user, an identification code for the end user, and/or an insurance code, for example.

The record further includes at least one telecommunication code 162 for contacting the end user. The at least one telecommunication code 162 can include a pager number, a telephone number, a cellular telephone number, a PCS number, and/or an electronic mail address, for example. Similarly, the record includes at least one telecommunication code 164 for a caregiver of the end user, at least one telecommunication code 166 for a family member of the end user, at least one telecommunication code 170 for medical personnel associated with the end user.

For each medicine prescribed for the end user, the record includes an identifier 172 of the medicine, an image or a designator thereof 174 associated with the medicine, a prescribed dosage 176 of the medicine, at least one time 180 at which the medicine is to be taken, an estimated amount 182 of medicine remaining in the prescription, and a compliance history 184 for taking the medicine. The identifier 172 can include a name of the medicine or an identification code for the medicine. The compliance history 184 can include times at which acknowledgment messages were received, and/or instances of noncompliance, for example. The estimated amount 182 can be formed with a down counter based upon an initial prescribed amount and the prescribed dosage 176. Alternatively, the estimated amount 182 can be received from the medical communication apparatus 20.

Optionally, the record includes a diagnostic history 186 for the end user. The diagnostic history 186 includes a plurality of diagnostic data measured using the diagnostic device 40 and received from the medical communication apparatus 20. The diagnostic history 186 can include a time and/or a date associated with each of the diagnostic data. In addition, the record can include an identifier 190 and an estimated remaining amount 192 of a medical supply associated with the diagnostic device 40.

As another option, the record can include a medical history 194 for the end user. The medical history 194 is received from medical personnel associated with the end user. The medical history 194 can be updated after an examination of the end user by the medical personnel. The medical history 194 can include results of medical examinations, medical tests, X-rays, and CAT scans, for example.

Figure 5:
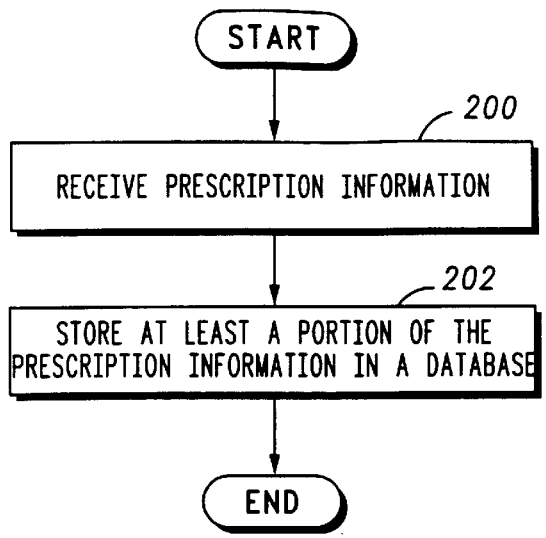
FIG. 5 is a flow chart of an embodiment of a first method performed by the medical database system.

FIG. 5 is a flow chart of an embodiment of a first method performed by the medical database system 24. As indicated by block 200, the method includes a step of receiving prescription information. The prescription information can be communicated from the communication unit 34 associated with medical personnel or the communication unit 36 associated with a pharmacy. The prescription information can be communicated to the medical database system 24 using a telephone network or a computer network such as the Internet or an intranet, for example. The prescription information can include an identifier of the end user, an identifier of the medicine, an image or a designator thereof associated with the medicine, a prescribed dosage of the medicine, at least one time at which the medicine is to be taken, an amount of medicine in the prescription, an identifier of the medical personnel, a telecommunication code for the medical personnel, an identifier of the pharmacy, and a telecommunication code for the pharmacy.

As indicated by block 202, the method includes a step of storing at least a portion of the prescription information in a database. This step can include a step of creating a record for the end user identified in the prescription if no such record exists. If a record for the end user already exists, the prescription information is stored in the record.

Figure 6:
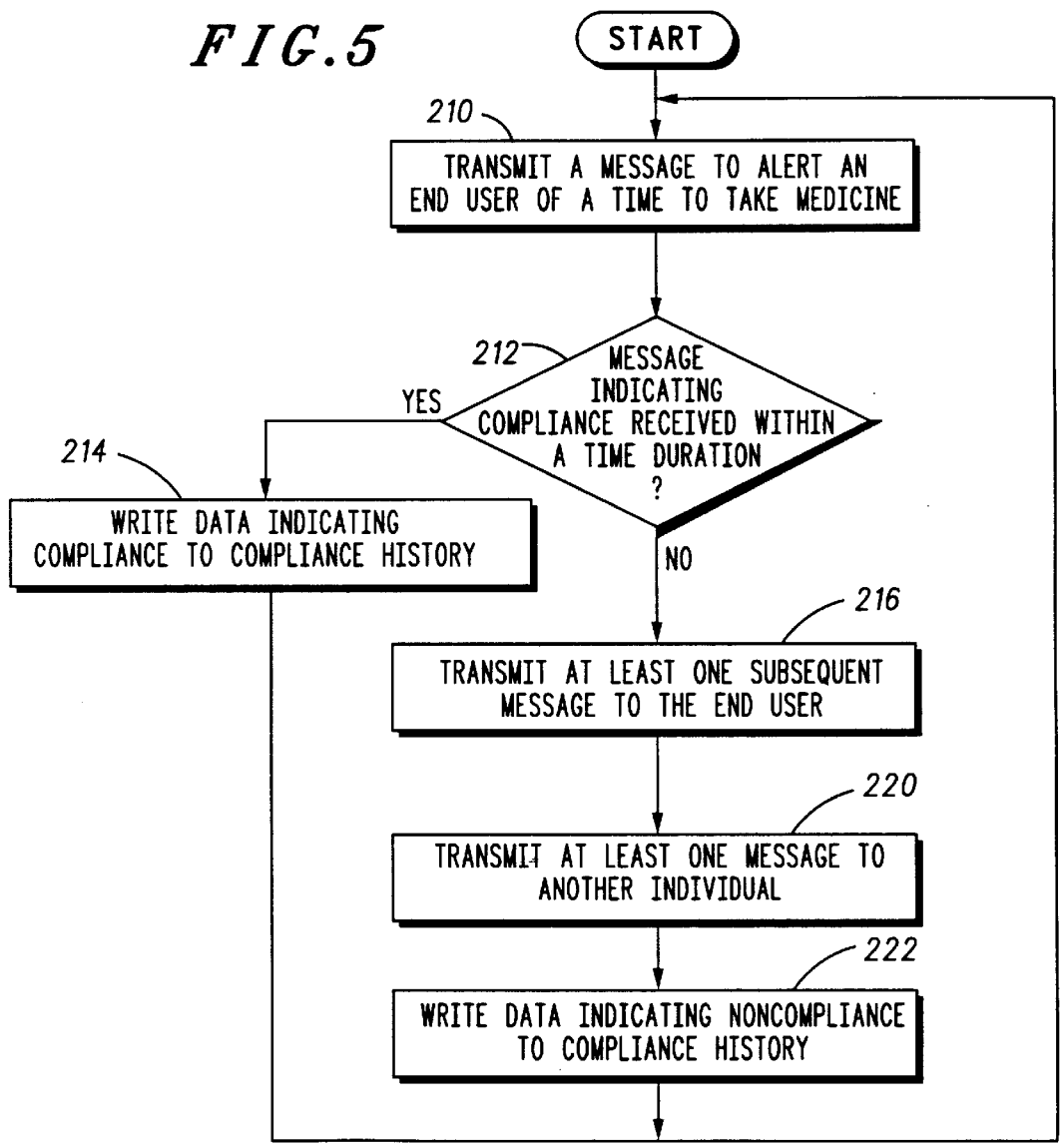
FIG. 6 is a flow chart of an embodiment of a second method performed by the medical database system.

FIG. 6 is a flow chart of an embodiment of a second method performed by the medical database system. As indicated by block 210, the method includes a step of transmitting a message to alert the end user of a time to take his/her medicine. The message is transmitted at a time based upon the prescription information stored in a record for the end user. The message is communicated to the medical communication apparatus of the end user using a first telecommunication code stored in the record. The message can include an identifier for each of at least one medicine, an image or a designator thereof for each medicine, and a dosage for each medicine.

As indicated by block 212, the method includes a step of determining whether a message indicating compliance with the prescription was received from the medical communication apparatus within a time duration. If the message indicating compliance is received within the time duration, a step of writing data indicative of compliance to the compliance history is performed as indicated by block 214.

If no message indicating compliance is received within the time duration, a step of transmitting at least one subsequent message to the end user is performed as indicated by block 216. This step can include sending a subsequent message to the medical communication apparatus and/or sending a message to the end user using another of the telecommunication codes stored in the record. Using the paging number, a paging message alerting of a time to take medicine can be communicated to the end user's pager. Using the telephone number, the cellular telephone number, and/or the PCS number, an automated voice message or fax message alerting of a time to take medicine can be communicated to the end user. Using the electronic mail address, an e-mail message alerting the end user of a time to take medicine can be communicated to a network access apparatus such as a personal computer.

Additionally, if no message indicating compliance is received within the time duration, a step of transmitting at least one message to another individual can be performed as indicated by block 220. This step can include sending a message to at least one of a caregiver for the end user, a family member of the end user, and the medical personnel using the telecommunication codes stored in the record. The message can include a paging message, an automated voice telephone message, a fax message, or an e-mail message indicating noncompliance of the end user with his/her prescription.

As indicated by block 222, the method includes a step of writing data indicative of noncompliance to the compliance history. After performing the step indicated by block 214 or the step indicated by block 222, flow of the method is directed back to block 210 to alert the end user, at a next prescribed time, to take his/her medicine.

FIG. 7 is a flow chart of an embodiment of a first method performed by a medical communication apparatus. As indicated by block 230, the method includes a step of receiving a message generated by the medical database system 24. The message can include an identifier for each medicine, an image or a designator thereof for each medicine, and a dosage for each medicine.

The message is communicated from the medical database system 24 to the medical communication apparatus using a paging service, a telephone network, or a computer network, for example. With reference to FIG. 2, the message is received by the receiver 54.

As indicated by block 232, the method includes a step of generating an alert indication. The alert indication is generated using the at least one output device 56 as directed by the processor 90.

As indicated by block 234, the method includes a step of displaying at least one image indicative of at least one medicine and a respective dosage therefor. The at least one image includes an image corresponding to the image 60 on the medicine container 52 containing the medicine 64 to be taken. The dosage is indicated either by displaying a number with the image or by displaying a number of like images corresponding to a number of pills to be taken.

The step of displaying is performed using a display device included in the output device 56, and is directed by the processor 90. If a designator of the image is received, the processor 90 retrieves the image from the storage medium 66 using the designator.

As indicated by block 236, the method includes a step of transmitting a signal to the medicine container 52 containing the medicine 64 to be taken. The signal is transmitted by the transmitter 72 as directed by the processor 90. The signal initiates the medicine container 52 to generate an indication for purposes described earlier. The signal can encode an identifier to identify which medicine container is to generate the indication.

As indicated by block 240, the method includes a step of receiving at least one user-initiated action. Each user-initiated action is received by the input device 70 described with reference to FIG. 2 or the buttons described with reference to FIG. 3. Typically, the at least one user-initiated action indicates that the end user has received the message and/or has complied with his/her prescription.

As indicated by block 242, the method includes a step of transmitting an acknowledgment message to the medical database system 24. The acknowledgment message can be sent in response to receiving the at least one user-initiated action. The acknowledgment message is indicative of reception of the message and/or compliance with the prescription. The acknowledgment message is transmitted using the transmitter 55.

FIG. 8 is a flow chart of an embodiment of a first method performed by a medicine container. As indicated by block 250, the method includes a step of receiving a signal from the medical communication apparatus. The signal is received by the receiver 76 described with reference to FIG. 2.

As indicated by block 252, the method includes a step of generating an indication if the signal identifies the medicine container. The processor 86 determines if the signal identifies the medicine container by comparing an identifier encoded in the signal with an identifier stored locally. The indication is generated by the indicator 82 under the direction of the processor 86 if the encoded identifier matches the locally-stored identifier.

FIG. 9 is a flow chart of an embodiment of a second method performed by a medicine container. As indicated by block 260, the method includes a step of sensing or estimating an amount of medicine remaining within the medicine container. The step of sensing the amount of medicine is performed by the sensor 84 and the processor 86 as described with reference to FIG. 2.

As indicated by block 262, the method includes a step of transmitting a signal associated with the amount of medicine to the medical communication apparatus 50. The signal is transmitted by the transmitter 80 under the direction of the processor 86. The signal can indicate the amount of medicine that remains, or can indicate that the amount of the medicine is at or below a predetermined threshold.

FIG. 10 is a flow chart of an embodiment of a second method performed by the medical communication apparatus 50. As indicated by block 270, the method includes a step of receiving a signal associated with an amount of medicine remaining in a medicine container. The signal is received by the receiver 74 described with reference to FIG. 2.

As indicated by block 272, the method includes a step of transmitting a message to the medical database system 24 based upon the amount of medicine remaining in the medicine container 52. The message is formed by the processor 90 to include an identifier of the end user, an identifier of the medicine, and optionally the amount of medicine. The processor 90 commands the transmitter 55 to transmit the message to the medical database system 24.

FIG. 11 is a flow chart of an embodiment of a third method performed by the medical database system 24. As indicated by block 280, the method includes a step of receiving a message such as a paging message associated with an amount of medicine that remains in a medicine container. Preferably, the message includes an identifier of the end user, an identifier of the medicine, and optionally the amount of medicine.

As indicated by block 282, the method includes a step of updating a record in the database upon receiving the message. This step can include updating the value of the estimated amount 182 of medicine remaining in the prescription as described with reference to FIG. 3.

As indicated by block 284, the method includes a step of sending a message to a pharmacy. The message can be sent to the communication unit 36 described with reference to FIG. 1. The message indicates either the amount of medicine remaining or that the amount of medicine is at or below a predetermined threshold. The message further identifies the end user. The pharmacy can utilize this information for automatically renewing selected prescriptions.

FIG. 12 is an illustration of an embodiment of a medical communication apparatus 300 coupled to a diagnostic device 302. The medical communication apparatus 300 is embodied by a two-way pager such as a Tango™ pager by Motorola, Inc. The two-way pager has a user interface 304, a display device 306, and a data port 310. The diagnostic device 302 is illustrated as a blood glucose meter having a display device 312, a user interface 314, a test strip holder 316, a test strip area 320, and a data port 322. The data port 310 is connected to the data port 322 by a cable 324.

The blood glucose meter measures a glucose level from a blood sample applied to a strip inserted into the test strip holder 316. The blood glucose meter communicates a signal associated with the glucose level from the data port 322 to the data port 310 via the cable 324. The two-way pager 300 receives the signal at the data port 310, and communicates a paging message associated with the glucose level to the medical database system 24.

FIG. 13 is an illustration of an embodiment of a medical communication apparatus 330 coupled to a data reader 332. The medical communication apparatus 330 includes a computer 334, a display 336, and input devices including a keyboard 340 and a mouse 342. The computer 334 includes a modem to communicate with an electronic network.

The data reader 332 includes a bar code reader to read at least one bar code 344 supported by a medicine container 346. The end user obtains information from a resource in the electronic network by reading a bar code using the data reader 332. The information is displayed on the display 336 or a printer.

The at least one bar code 344 can encode a variety of information, such as those described with reference to the machine-readable data 94 in FIG. 2. Each type of encoded information can be read to initiate a corresponding series of steps.

In response to reading data identifying the end user from the at least one bar code 344, the medical communication apparatus 330 can download information from the end user's record into the medical database system 24.

In response to reading data identifying the medicine in the medicine container 346 or data for obtaining information about the medicine, the medical communication apparatus 330 can download information regarding the medicine. The information can include side effects of the medicine and interactions with other medicines, for example.

In response to reading data identifying a pharmacy from which the medicine was procured, the medical communication apparatus 330 can display the name, the address, and the telephone number of the pharmacy.

In response to reading data for establishing a communication link to the pharmacy, the medical communication apparatus 330 can either: link to a web page for the pharmacy, initiate a telephone call to the pharmacy, or initiate an e-mail message to the pharmacy.

In response to reading data identifying medical personnel which prescribed the medicine, the medical communication apparatus 330 can display the name, the address, and the telephone number of the medical personnel.

In response to reading data for establishing a communication link to the medical personnel, the medical communication apparatus 330 can either: link to a web page for the medical personnel, initiate a telephone call to the medical personnel, or initiate an e-mail message to the medical personnel.

It is noted that the medical communication apparatus can include any of the embodiments of a network access apparatus described in the related applications incorporated by reference into this disclosure. Additionally, the machine-readable data and/or the substrate can be formed in accordance with any of the embodiments of network navigation devices described in the related applications incorporated by reference. Further, the data reader 332 can include any of the data readers described in the related applications incorporated by reference. Still further, the medical communication apparatus can link to a resource in an electronic network in accordance with methods and systems described in the related applications incorporated by reference.

It is noted that, in addition to monitoring compliance to prescriptions, the methods described herein can be modified to monitor compliance in the end user 22 performing medical diagnostic procedures using the diagnostic device 40. Further, in addition to automatically renewing prescriptions by monitoring an amount of medicine which remains and communicating a message to a pharmacy, the methods described herein can be modified to automatically reorder any medical supply for the end user 22 by monitoring an amount of the medical supply which remains.

Thus, there has been described herein several embodiments including preferred embodiments of a medical communication system.

Because the various embodiments of the present invention utilize a graphical representation associated with a medicine container, they provide a significant improvement in simplifying the identification of the medicine therein.

Additionally, the various embodiments of the present invention as herein-described maintain a compliance history so that medical personnel can monitor the end user's compliance with a prescription.

Further, by communicating a message associated with an amount of medicine which remains in a prescription to a pharmacy, the pharmacy can automatically refill selected prescriptions.

It will be apparent to those skilled in the art that the disclosed invention may be modified in numerous ways and may assume many embodiments other than the preferred form specifically set out and described above.

Accordingly, it is intended by the appended claims to cover all modifications of the invention which fall within the true spirit and scope of the invention.

What is claimed is:

1. A medical communication method comprising the steps of:

generating a message to alert an individual to take a first medicine and a second medicine;

transmitting the message to a wireless pager for the individual;

receiving the message using the wireless pager;

generating an alert indication using the wireless pager;

simultaneously displaying, using the wireless pager, a first graphical indication of a first dosage of the first medicine which is to be taken by the individual, and a second graphical indication of a second dosage of the second medicine which is to be taken by the individual, wherein the first dosage of the first medicine consists of N pills, wherein the first graphical indication comprises N images of an icon disposed on a container of the first medicine, and wherein N is at least two; and transmitting a subsequent message to a communication unit other than the wireless pager upon determining a noncompliance condition for the individual.

2. The medical communication method of claim 1 wherein the wireless pager is a two-way wireless pager.

3. A medical communication method comprising the steps of:

generating a message to alert an individual to take a first dosage of a first medicine, and to graphically indicate to the individual the first dosage of the first medicine which is to be taken, wherein the message includes an image of an icon disposed on a container of the first medicine; and transmitting a subsequent message upon determining a noncompliance condition for the individual.

4. The medical communication method of claim 3 further comprising the step of transmitting the message using a wireless paging system.

5. The medical communication method of claim 3 further comprising the step of transmitting the message using a computer network.

6. A medical communication method comprising the steps of:

generating a message to alert an individual to take a first dosage of a first medicine, and to graphically indicate to the individual the first dosage of the first medicine which is to be taken, wherein the message includes a designator of an image of an icon disposed on a container of the first medicine; and transmitting a subsequent message upon determining a noncompliance condition for the individual.

7. The medical communication method of claim 6 further comprising the step of:

transmitting the message using a wireless paging system.

8. The medical communication method of claim 6 further comprising the step of:

transmitting the message using a computer network.

* * * * *